United States Patent [19]
Ohnishi et al.

[11] Patent Number: 4,578,400
[45] Date of Patent: Mar. 25, 1986

[54] THERAPEUTIC COMPOSITION AND METHOD FOR TREATMENT OF CARDIOVASCULAR DISEASES

[75] Inventors: Haruo Ohnishi, Funabashi; Kazuo Yamaguchi, Koganei; Yasuo Suzuki, Kawaguchi; Nobuo Mochida, Suginami, all of Japan

[73] Assignee: Mochida Pharmaceutical Co., Ltd., Tokyo, Japan

[21] Appl. No.: 680,593

[22] Filed: Dec. 11, 1984

Related U.S. Application Data

[63] Continuation of Ser. No. 506,216, Jun. 21, 1983, abandoned.

[30] Foreign Application Priority Data

Jun. 28, 1982 [JP] Japan ................... 57-111183

[51] Int. Cl.$^4$ ............... A61K 31/35; A61K 31/20
[52] U.S. Cl. ...................... 514/460; 514/552; 514/558
[58] Field of Search ............ 514/552, 558, 460

[56] References Cited

U.S. PATENT DOCUMENTS 4,250,062  2/1981  Kaiser ..................... 252/522 R
4,357,315  11/1982 Boden ....................... 424/49

FOREIGN PATENT DOCUMENTS 1417119 12/1975 United Kingdom .

OTHER PUBLICATIONS

"Antibacterial Activity of Myrmicacin", pp. 262–266, by Toshihiko Iizuka, Tsukasa Iwadare and Kazuhiko Orito, entitled *Antibacterial Activity of Myrmicacin and Related Compounds on Pathogenic Bacteria in Silkworm Larve, Streptococcus Faecalis AD-4*.
Urbach et al., J. Dairy Res., 39, 35–47 (1972).
Gert Als, *Food Manufacture*, "Delta-Lactones in Flavouring", vol. 48, pp. 31–32, Jan. 1973.
C. J. Wyatt et al., *Lipids*, "The Lactone Precursor in Fresh Milk Fat: Indentification of the Hydroxy Fatty Acids[1]", vol. 2, pp. 208–211 (1967).
Wyatt, C. J. et al., J. Daily Science, 50, 1760–1763, (1967).
J. E. Kinsella, Food Technology, 82–98, (1975).

Primary Examiner—Leonard Schenkman
Attorney, Agent, or Firm—Parkhurst & Oliff

[57] ABSTRACT

A therapeutic agent for the treatment of cardiovascular diseases which contains as the effective component at least one compound selected from the group consisting of 5-hydroxydecanoic acid, a salt thereof, an ester thereof and δ-decalactone, which is a lactone of 5-hydroxydecanoic acid.

55 Claims, No Drawings

THERAPEUTIC COMPOSITION AND METHOD FOR TREATMENT OF CARDIOVASCULAR DISEASES

This is a continuation of application Ser. No. 506,216 filed June 21, 1983 now abandoned.

BACKGROUND OF THE INVENTION

The present invention relates to a therapeutic agent and method for treatment of cardiovascular diseases. More particularly, the present invention relates to a therapeutic agent for cardiovascular diseases that contains as the effective ingredient at least one compound selected from the group consisting of 5-hydroxydecanoic acid, a salt thereof, an ester thereof and δ-decalactone which is a lactone of 5-hydroxydecanoic acid, and a method for treating cardiovascular diseases with such a therapeutic agent.

Cardiovascular diseases and cancer are the most common natural causes of death. The cardiovascular diseases include many serious diseases which involve the cardiac and vascular systems, such as atherosclerosis, ischemic heart diseases, cardiac failure, cardiac shock, arrhythmia, hypertension, cerebral vascular diseases and peripheral vascular diseases. Atherosclerosis most often occurs as a complication of hyperlipidemia and can be treated with antihyperlipidemic agents. Ischemic heart disease, cardiac failure, cardiac shock, cerebral vascular disease, peripheral vascular disease, hypertension, arrhythmia and arteriosclerosis may be fatal because ischemia develops in various organs such as the heart, brain and the walls of blood vessels. The ischemia damages the organs in which it develops because it impairs the functions of mitochondria that produce adenosine triphosphate (ATP), which is a phosphate compound with high energy potential serving as an energy source for the constituent cells of these organs. The resulting functional damage of organs can be fatal if it occurs in vital organs such as the heart, brain and blood vessels. It is therefore important for treating these diseases to restore the functional impairment of mitochondria caused by ischemia. Antiarrhythmic agents have been used to treat ischemic heart disease and arrhythmia, but their use with patients with possible cardiac failure has been strictly limited because these agents may cause cardiac arrest by their cardiodepressant effects.

The cardiovascular diseases named above may develop independently, but more often than not they occur in various combinations. For example, ischemic heart diseases are frequently accompanied by arrhythmia and cardiac failure, and complications of cerebrovascular disorder with hypertension are well known. Atherosclerosis is often complicated by one or more cardiovascular diseases and can make the patient seriously ill.

Cardiovascular diseases, which are often complicated by other cardiovascular diseases, have often been treated so far with a combination of multiple drugs, each of which is specific for a single disease. However, drug-therapy employing multiple agents presents problems for both doctors and patients: doctors always consider compatibilities and contraindications of drugs, and patients suffer both mental and physical distresses due to complicated administration of various drugs and high incidence of adverse reactions. Therefore, it has long been desired to develop a therapeutic agent that has overall pharmacological activities against cardiovascular diseases and which can be employed in the treatment of these diseases with high efficacy.

SUMMARY OF THE INVENTION

One object of the present invention is to provide a therapeutic agent for comprehensive treatment of a wide spectrum of cardiovascular diseases, such as hypertension, atherosclerosis and ischemic heart diseases.

Another object of the present invention is to provide a therapeutic agent for individual cardiovascular diseases.

These objects can be achieved by a therapeutic agent that contains as the effective ingredient at least one compound selected from the group consisting of 5-hydroxydecanoic acid, a salt thereof, an ester thereof, and δ-decalactone, which is a lactone of 5-hydroxydecanoic acid.

The therapeutic agent of the present invention is advantageous in that it can be used for comprehensive treatment of cardiovascular diseases, whose pathogenic factors are more often than not multiple and complicated, without using a combination of many drugs, and in that the agent can also be used for the treatment of individual cardiovascular diseases.

DETAILED DESCRIPTION OF THE INVENTION

As a result of long studies to develop a therapeutic agent that is free from the defects of the conventional drugs for treating cardiovascular diseases, the present inventors have found that 5-hydroxydecanoic acid (5—HDA), its salt, its ester and δ-decalactone, which is a lactone of 5—HDA, have several independent pharmacological activities: (a) therapeutic effect on hyperlipidemia which is the primary cause of atherosclerosis, (b) suppressive effect on impairment of mitochondria functions caused by ischemia, and (c) an anti-arrhythmic effect that is not accompanied by cardiodepressant effects.

The 5-hydroxydecanoic acid (I) and δ-decalactone (II) are known compounds and have the following formulae:

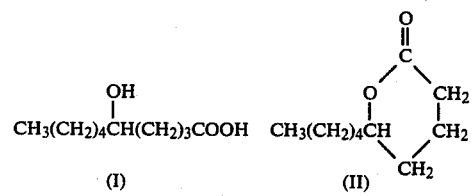

5-Hydroxydecanoic acid is described by Wyatt, C. J., et al, (J. Daily Science, 50, 1760-1763, 1967) and may be prepared from a commercially available δ-decalatone which is a well known flavouring for foods (Als. G. Food Mfr., 48, 31-32, 1973). δ-Decalactone is stirred in an aqueous solution containing an equimolar amount of alkali and the reaction mixture is extracted to obtain 5-hydroxydecanoic acid with a solvent under acidic conditions. It is also known that the so prepared 5-hydroxydecanoic acid can be readily converted to its lactone, δ-decalactone (Wyatt, C. J., et al., Lipids, 2, 208-211, 1967).

The 5-hydroxydecanoic acid so produced may be converted to pharmacologically acceptable salts. Suitable salts include salts with metals such as sodium, potassium and lithium; salts with organic bases such as dimethylamine and ammonium; and salts with amino acids such as glycine, lysine and arginine. The 5-hydroxydecanoic acid may also form alkyl esters such as methyl, ethyl and propyl esters; di- or tri-valent hydroxyalkyl esters with ethylene glycol, propylene glycol, butanediol and glycerol and derivatives thereof, and esters with aromatic compounds such as phenyl, naphthyl, pyridyl and quinolyl derivatives. Esters of 5-hydroxydecanoic acid may be produced by reacting 5-hydroxydecanoic acid with corresponding alcohols.

The physicochemical data of 5-hydroxydecanoic acid, δ-decalactone and typical salts and esters of 5-hydroxydecanoic acid are listed in Table 1.

conventional technique using any conventional pharmaceutical carrier, vehicle or excipient.

Examples of solid carriers and excipients usable advantageously herein include common excipients such as lactose, mannitol, corn starch and potato starch; binders such as crystalline cellulose, cellulose derivatives, arabic gum, corn starch and gelatin; disintegrators such as corn starch, potato starch and calcium carbohydroxymethylcellulose; and lubricants such as talc and magnesium stearate. Examples of liquid carriers usable advantageously herein include distilled water for injection, physiological saline solution, vegetable oils for injection and glycols such as propylene glycol and polyethylene glycol.

TABLE 1

| Abbreviation | Compound | Analytical data | Properties |
|---|---|---|---|
| 5-HDA | 5-hydroxy-decanoic acid | IR spectrum (liquid film $cm^{-1}$) 3400,2940,1710, 1460,1410,1250; $^{13}$C-NMR spectrum ($CDCl_3$,δ;ppm) 13.86, 20.71,22.45,25.10, 31.73,33.79,36.12, 36.90,71.32,177.59 | colorless oil, easily soluble in methanol, acetone, chloroform and benzene, sparingly soluble in water |
| 5-HDA-Na | Sodium 5-hydroxy-decanoate | m.p. 156~157° C.; IR spectrum (KBr, $cm^{-1}$) 3370,2930,1560,1450, 1420; $^{13}$C-NMR spectrum ($D_2O$,δ;ppm) 14.43, 23.05,25.74,32.38, 37.05,37.41,38.43, 71.95,183.82 | colorless crystalline powder, easily soluble in water, methanol and acetone, sparingly soluble in benzene, chloroform and hexane |
| δ-DL | δ-decalactone | b.p. 118.5~119.5° C./1 mm Hg; IR spectrum (liquid film $cm^{-1}$) 2950,2875, 1740,1470,1250,1160, 1140,940; $^{13}$C-NMR spectrum ($CDCl_3$δ;ppm) 13.28,17.78,21.85, 23.94,27.11,28.73, 30.95,35.14,79.70, 171.02 | colorless liquid, easily soluble in hexane, benzene, acetone, chloroform and methanol, insoluble in water |
| 5-HDAE | Ethyl-5-hydroxy-decanoate | IR spectrum (liquid film $cm^{-1}$) 3450,2950, 2875,1745,1470,1390, 1170 | colorless oil, easily soluble in methanol, acetone, chloroform and benzene, sparingly soluble in water |
| 5-HDA-DHP | 2',3'-dihydroxy-propyl-5-hydroxydecanoate | IR spectrum (liquid film $cm^{-1}$) 3450,2950, 2880,1740,1470,1390, 1180 | colorless oil, easily soluble in methanol, acetone and chloroform, and soluble in water |

The therapeutic agent of the present invention has multiple pharmacological effects on the cardiovascular system, so it can be used for comprehensive treatment of cardiovascular diseases which often complicate other cardiovascular diseases. Furthermore, the multiple effects of the agent can be individually used to treat specific cardiovascular diseases: its antihyperlipidemic effect can be used to treat atherosclerosis, its antiarrhythmic effect may be used to treat arrhythmia, and its activity to suppress the malfunction of mitochondria can be used to treat ischemic disorders.

The therapeutic agent of the present invention is used in an amount of 5 to 5,000 mg daily for an adult. For oral administration, the preferred dose is from 100 to 5,000 mg, and for injection and administration on mucous membranes, the preferred dose is from 5 to 500 mg. The exact dose may vary according to the route of administration and the severity of the disease. The active compounds may be present alone or in combination.

Pharmaceutical preparations can be produced from the therapeutic agent of the present invention by any Pharmaceutical preparations include oral preparations such as capsules, tablets, granules, powders and oral liquid formulations; and rectal preparations such as rectal suppositories. As injectable forms, emulsions for injection may be prepared from 5—HDA, esters of 5—HDA, which are poorly soluble in water, and δ-DL, and aqueous solutions for injection may be prepared from 5—HDA—Na or water-soluble esters of 5—HDA. The compounds may also be administered by application on mucous membranes.

The efficacy, safety, usage and dosage of 5—HDA, 5—HDA—Na, 5—HDAE, 5—HDA—DHP and δ-DL, and the methods for preparing therapeutic agents containing them are described in the following experiments and examples.

EXPERIMENT 1

Effect on chloroform-induced arrhythmia

The procedure described by J. W. Lawson (J. Pharmacol. Exp. Ther., 160, 22-31, 1967) was followed.

Male ddy mice weighing 15 to 20 g were divided into groups of 10 animals, and orally administered the compounds listed in Table 2. Fifteen minutes later, the mice were put in a gas-tight container filled with chloroform vapor. When they stopped breathing, they were thoracotomized to examine the occurrence of ventricular fribrillation. The results are noted in Table 2 as percent occurrence of ventricular fibrillation.

TABLE 2

| Test compound | Dosage (mg/kg) | Percent occurrence of ventricular fibrillation |
| --- | --- | --- |
| Control | | 100 |
| 5-HDA | 50 | 60 |
| | 100 | 30* |
| 5-HDA-Na | 50 | 50 |
| | 100 | 30* |
| 5-HDAE | 100 | 30* |
| 5-HDA-DHP | 100 | 20* |
| δ-DL | 100 | 30* |
| Lidocaine | 10** | 40 |

*P <0.05
**Lidocaine was injected intraperitoneally 5 minutes before the application of chloroform.

The data shows that 5—HDA, 5—HDA—Na, 5-HDAE, 5—HDA—DHP and δ-DL administered at a dosage of 100 mg/kg exhibited significant anti-arrhythmic effects which were more potent than lidocaine. The data also shows that 5—HDA, 5—HDA—Na, 5—HDAE, 5—HDA—DHP and δ-DL exhibit significant effects when administered orally which is preferred in practical treatment. To the contrary, since lidocaine is not effective by oral administration, lidocaine should be administered by injection.

EXPERIMENT 2

Effect on ouabain induced arrhythmia

The procedure described in Matsubara et al. (Folia Pharmacologica Japonica, 72, 557-571, 1976) was followed.

Male hartley guinea pigs were divided into groups of 8 animals and anesthetized with intraperitoneal urethane. Three groups were orally administered 5—HDA—Na, 5—HDAE and 5—HDA—DHP dissolved in distilled water. Another group was intravenously injected with 5—HDA—Na dissolved in physiological saline. One group was orally administered δ-DL emulsified in 5% aqueous arabic gum solution. One group was injected intravenously with lidocaine dissolved in physiological saline. For the respective routes of administration, control groups were administered the solvents used in administration of the test compounds. Thirty minutes after the oral administration and one minute after the intravenous injection, ouabain was infused into the jugular vein at a rate of 5 µg/kg/min until extrasystole, ventricular fibrillation and cardiac arrest appeared on a standard limb lead II of ECG. The results are shown in Table 3, with the time necessary for the respective symptoms to occur in the control groups taken as 100.

TABLE 3

| Test compound | Route of administration | Dosage (mg/kg) | Extrasystole** | Ventricular fibrillation** | Cardiac arrest** |
| --- | --- | --- | --- | --- | --- |
| 5-HDA-Na | oral | 50 | 118 | 126* | 134* |
| | | 100 | 160 | 144* | 136* |
| | i.v. | 20 | 146 | 140* | 132* |
| 5-HDAE | oral | 100 | 151 | 146* | 132* |
| 5-HDA-DHP | oral | 100 | 193 | 139* | 122 |
| δ-DL | oral | 100 | 157 | 137* | 140* |
| Lidocaine | i.v. | 10 | 133 | 129* | 118 |

*P <0.05
**The relative time for the respective symptoms to occur.

The above data show that 5—HDA—Na, 5—HDAE, 5—HDA—DHP and δ-DL exhibited significant antiarrhythmic effects.

EXPERIMENT 3

Antiarrhythmic effects on myocardial infarction

The method described by Shinohara (Jap. Circul. J., 32, 1269-1281, 1968) was used. Dogs were divided into groups of 5 animals, anesthetized with intravenous pentobarbital and were thoracotomized under artificial respiration, and a platinum bipolar electrode was inserted on the wall of the right atrium. Then the sinus node was crushed and the animals were subjected to pacing (2.5 Hz, 3 msec, 3.5-8 V) with an electronic stimulator. The left anterior descending coronary artery was doubly ligated at a site 2 cm away from its origin (A. S. Harris, Circulation, 1, 1318, 1950). Then 5—HDA—Na and lidocaine were injected into the femoral vein of the respective dogs. Using an electrode inserted in an ischemic zone in the left ventricle, the animals were given 15 to 20 successive electrical shocks before the ligation and 30 minutes after the ligation and administration. The threshold level necessary for inducing ventricular fibrillation was determined for each group of animals and shown in Table 4, with the values before the ligation taken as 100.

TABLE 4

| Test compound | Dosage (mg/kg) | Threshold level for inducing ventricular fibrillation | |
| --- | --- | --- | --- |
| | | Before ligation | 30 min after ligation |
| Control | | 100 | 41 |
| 5-HDA-Na | 0.3 | 100 | 67 |
| | 1.0 | 100 | 70* |
| | 3.0 | 100 | 79* |
| Lidocaine | 0.3 | 100 | 68 |
| | 1.0 | 100 | 84* |

*P <0.05

The threshold level for inducing ventricular fibrillation was decreased by ligating the coronary artery, but following the administration of 5—HDA—Na it was increased in a dose-dependent manner. This reflects the antiarrhythmic effect of 5—HDA—Na and its ability to suppress the impairment of mitchondria function.

EXPERIMENT 4

Inhibition of the activity of 3-hydroxy-3-methylglutaryl coenzyme A (HMG-Co A) reductase The activity of HMG—CO A reductase, which is the ratedetermining enzyme for biosynthesis of cholesterol, was measured by the method of D. J. Shapiro (Analytical Biochemistry, 3, 383-390, 1969) using a rat liver microsome as the source of the enzyme. The amount of 5—HDA—Na and Compactin, a well-known HMG—Co A reductase inhibitor, necessary for inhibiting the enzymatic activity by 30% ($IC_{30}$) are listed in Table 5.

TABLE 5

| Test compound | $IC_{30}$ |
|---|---|
| 5-HDA-Na | $1 \times 10^{-4}$ M |
| Compactin | $3 \times 10^{-5}$ M |

The data clearly shows the activity of 5—HDA—Na to inhibit HMG—Co A.

EXPERIMENT 5

Lowering serum lipid levels in Triton-induced hyperlipidemic rats

Male Wistar rats weighing 200–250 g were divided into groups of 5 animals and intravenously injected with 200 mg/kg of Triton WR-1339 dissolved in physiological saline. After 10 hours, blood samples were drawn to determine the serum levels of total cholesterol and triglyceride. The compounds listed in Table 5 were orally administered to the animals four times: immediately, 3, 6, and 9 hours after the administration of Triton WR-1339. The results are listed in Table 6 as inhibition rate against the values for the control group.

TABLE 6

| Test compound | Dosage (mg/kg) | Total cholesterol | Triglyceride |
|---|---|---|---|
| 5-HDA-NA | 100 | 20%* | 15%* |
| 5-HDAE | 100 | 19%* | 17%* |
| 5-HDA-DHP | 100 | 19%* | 18%* |
| δ-DL | 100 | 23%* | 11%* |
| Clofibrate | 100 | 14%* | 16%* |

*$P < 0.05$

As is clear from the above data, 5—HDA—Na, 5—HDAE, 5—HDA—DHP and δ-DL exhibited antilipidemic effects that were equipotent to or stronger than the effect of the known anti-lipidemic agent, Clofibrate.

EXPERIMENT 6

Lowering serum cholesterol levels in hyperlipidemic rabbits

Male Japanese white rabbits weighing about 2.5 kg were fed on a solid diet containing 1% cholesterol (RC-4, Nippon Crea Co., Ltd.) for 10 weeks until hypercholesterolemia fully developed. The rabbits were then divided into groups of 5 animals, and 5—HDA—Na or δ-DL was orally admininistered daily for 7 days, either as a solution or as an emulsion in 5% aqueous arabic gum. Three hours after the last administration, blood was drawn to determine the serum level of cholesterol. The results are shown in Table 7.

TABLE 7

| Test compound | Dosage (mg/kg) | Total serum cholesterol (mg/dl) |
|---|---|---|
| Control | | 1,394 |
| 5-HDA-Na | 100 | 1,165* |
| δ-DL | 100 | 1,141* |

*$P < 0.05$

Obviously, 5—HDA—Na and δ-DL lowered the serum level of total cholesterol.

EXPERIMENT 7

Inhibition of the decrease in respiratory capacity of myocardial mitochondria

According to the method of Hagiwara (Biochem. Biophys. Acta, 46, 134–142, 1961), mitochondria fractions were prepared from the myocardium isolated from male Wistar rats weighing about 300 g. The respiratory capacity of the mitochondria was measured by polarography with an oxygen electrode (TA-100, Yanagimoto), with sodium glutamate and ADP being successively added to give final concentrations of 50 mM and 4 mM, respectively. Defective mitochondria were prepared by leaviang the mitochondria fractions at 0° C. for 24 hours, and 5—HDA—Na was added to determine its ability to inhibit the decrease in the respiratory capacity of the myocardial mitochondria, which is proportional to the rate of ATP production. The results are shown in Table 8.

TABLE 8

| Test group | Concentration (M) | ATP production rate mM/mg-protein/min |
|---|---|---|
| Normal mitochondria | | 515 |
| Defective mitochondria | | 204 |
| Defective mitochondria + 5-HDA-Na | $10^{-5}$ | 220* |
| | $10^{-4}$ | 265* |

*$P < 0.05$

The decrease in ATP production in the defective mitochondria was significantly inhibited by addition of 5—HDA—Na.

EXPERIMENT 8

Acute toxicity

Male ddy mice weighing about 25 g were divided into groups of 10 animals and orally administered once with 3 g/kg of 5—HDA, 5—HDA—Na, 5—HDAE, 5—HDA—DHP or δ-DL, or intraperitoneally injected once with 1 g/kg of said compounds. The mice were observed for one week, and no abnormality occurred and no animal died.

The above results show that the 5—HDA of the present invention, its salts or lower alkyl esters, as well as its lactone, δ-DL, can be used in pharmacologically effective doses without presenting any hazard to humans. Furthermore, these compounds have antiarryhthmic and antilipidemic effects as well as the ability to restore the impaired functions of mitochondria. Therefore, they will prove very effective in the treatment of cardiovascular diseases in humans, such as arteriosclerosis, ischemic heart diseases, cardiac failure, cardiac shock, arrhythmia, hypertension, cerebral vascular diseases, peripheral vascular diseases, and hyperlipidemia.

EXAMPLE 1

Preparation of tablets

Five hundred grams of 5—HDA—Na were intimately mixed with 320 g of lactose and 150 g of potato starch. To the resulting mixture, 15 g of aqueous polyvinyl alcohol were added, and granules were prepared from the mixture by wet granulation. The granules obtained were dried and mixed with 15 g of magnesium stearate. The mixture was compressed into tablets each weighing 200 mg.

EXAMPLE 2

Liquid preparation for oral administration

| 5-HDA-Na | 50 g |
|---|---|
| Liquid glucose | 300 g |
| Sucrose | 250 g |
| Preservative* | a very small amount |
| Purified water | to make 1,000 ml |

*As the preservative, those conventionally used for oral liquid preparations such as sodium dehydroacetate, butyl p-hydroxybenzoate, chlorobutanol, benzyl alcohol, etc., may be suitably employed.

EXAMPLE 3

Powder

A 10% powder was prepared from an intimate mixture of the following components:

| 5-HDA | 100 g |
|---|---|
| Lactose | 890 g |
| Magnesium stearate | 10 g |
| Total | 1,000 g |

EXAMPLE 4

Capsule

A uniform mixture of 400 g of 5—HDA—Na, 585 g of lactose and 15 g of magnesium stearate was filled into No. 1 hard gelatin capsules to contain 500 mg of said mixture in each capsule.

EXAMPLE 5

Suppository

One hundred grams of 5—HDA—Na that had been ground in a mortar into fine particles were mixed with 180 g of polyethylene glycol 1500 and 720 g of polyethylene glycol 4000. The mixture was made into suppositories weighing 500 mg each, by a melting method.

EXAMPLE 6

Soft capsule

Glycerin was added to 500 g of δ-DL to make 1,000 ml and intimately mixed. Soft capsules were punched from gelatin sheets each containing 0.2 ml of the resulting liquid mixture.

EXAMPLE 7

Aqueous solution for injection

Fifty grams of 5—HDA—Na were dissolved in distilled water for injection. To the solution, another volume of distilled water for injection was added to make 1,000 ml. The resulting aqueous solution was sterilized with a membrane filter, and the filtrate was filled in glass containers in 2 ml portions and lyophilized. The containers were then sealed.

EXAMPLE 8

Aqueous solution for injection

One hundred grams of 5—HDA—DHP were dissolved in distilled water for injection. To the solution, another volume of distilled water for injection was added to make 2,000 ml. The resulting aqueous solution was sterilized with a membrane filter, and the filtrate was filled in ampules in 2 ml portions by a conventional method. The ampules were then sealed.

EXAMPLE 9

Emulsion for injection

To a mixture of 100 g of δ-DL and 200 g of polyoxyethylene sorbitan monooleate, distilled water for injection was added to make 2,000 ml. The resulting mixture was emulsified with an ultrasonic homogenizer to make a uniform emulsion. The resulting emulsion was heated at 110° C. under 1.055 kg/cm² for 20 minutes and filled in ampules in 2 ml portions. The ampules were then sealed.

What is claimed is:

1. A composition for the treatment of cardiovascular diseases comprising a unit dosage form selected from the group consisting of oral preparation, injection and rectal suppository, said unit dosage containing 5-5000 mg of at least one active compound selected from the group consisting of 5-hydroxydecanoic acid, a salt thereof, and a methyl, ethyl and dihydroxypropyl ester thereof and one or more pharmaceutically acceptable excipients.

2. A composition according to claim 1, said composition being in a unit dosage form selected from the group consisting of capsules, tablets, granules, powders and oral liquid formulations.

3. A composition according to claim 2, wherein said unit dosage form is capsules.

4. A composition according to claim 1, said composition being in a unit dosage form selected from the group consisting of an aqueous solution for injection, an emulsion for injection and a lyophilized preparation for injection.

5. A composition according to claim 4, wherein said excipient comprises physiological saline.

6. A composition according to claim 1, said composition being in a unit dosage form of a rectal suppository.

7. A composition according to claim 1, wherein said single unit dosage contains 100-5,000 mg of said active compound.

8. A composition according to claim 1, wherein said unit dosage contains 5-500 mg of said active compound.

9. A composition according to claim 1, wherein said composition is contained in an ampule for injection.

10. A composition according to claim 9, wherein said excipient comprises distilled water for injection.

11. A composition according to claim 1, wherein said excipient comprises a syrup.

12. A composition according to claim 1, wherein said composition is emulsified.

13. A composition according to claim 1, wherein said excipient comprises glycols.

14. A composition according to claim 13, wherein said glycols are selected from the group consisting of propylene glycol and polyethylene glycol.

15. A composition for the treatment of cardiovascular diseases comprising a unit dosage form selected from the group consisting of oral preparation, injection and rectal suppository, said unit dosage form containing 5-5000 mg of at least one active compound selected from the group consisting of 5-hydroxydecanoic acid, a salt thereof and a methyl, ethyl and dihydroxylpropyl ester and one or more pharmaceutically acceptable excipients, said unit dosage form being selected from the group consisting of capsules, tablets, granules, powders, rectal suppositories, lyophilized preparations for injection and preparations for injection containing physiological saline solution or vegetable oils.

16. A composition for the treatment of cardiovascular diseases comprising a unit dosage form selected from the group consisting of oral preparation, injection and rectal suppository, said unit dosage containing 5–5000 mg of at least one active compound selected from the group consisting of 5-hydroxydecanoic acid, a salt thereof, a methyl, ethyl and dihydroxypropyl ester thereof and δ-decalactone and one or more pharmaceutically acceptable excipients, said composition having 5–50% by weight of the active components.

17. A composition according to claim 16, said composition being in a unit dosage form selected from the group consisting of capsules, tablets, granules, powders and oral liquid formulations.

18. A composition according to claim 16, said composition being in a unit dosage form selected from the group consisting of an aqueous solution for injection, an emulsion for injection and a lyophilized preparation for injection.

19. A composition according to claim 16, said composition being in a unit dosage form of a rectal suppository.

20. A composition according to claim 17, wherein said unit dosage form is capsules.

21. A composition according to claim 16, wherein said unit dosage contains 100–5,000 mg of said active compound.

22. A composition according to claim 16, wherein said unit dosage contains 5–500 mg of said active compound.

23. A composition according to claim 18, wherein said excipient comprises physiological saline.

24. A composition according to claim 16, wherein said composition is contained in an ampule for injection.

25. A composition according to claim 24, wherein said excipient comprises distilled water for injection.

26. A composition according to claim 16, wherein said excipient comprises a syrup.

27. A composition according to claim 16, wherein said composition is emulsified.

28. A composition according to claim 16, wherein said excipient comprises glycols.

29. A composition according to claim 28, wherein said glycols are selected from the group consisting of propylene glycol and polyethylene glycol.

30. A composition for the treatment of cardiovascular diseases comprising a unit dosage form selected from the group consisting of oral preparation, injection and rectal suppository, said unit dosage containing 5–5000 mg of at least one active compound selected from the group consisting of 5-hydroxydecanoic acid, a salt thereof, a methyl, ethyl and dihydroxypropyl ester thereof and δ-decalactone and one or more pharmaceutically acceptable excipients, said composition having 5–50% by weight of the active components, said unit dosage form being selected from the group consisting of capsules, tablets, granules, powders, rectal suppositories, lyophilized preparations for injection and preparations for injection containing physiological saline solution or vegetable oils.

31. A composition for the treatment of cardiovascular diseases comprising a unit dosage form selected from the group consisting of oral preparation, injection and rectal suppository, said unit dosage containing 5–5000 mg of at least one active compound selected from the group consisting of 5-hydroxydecanoic acid, a salt thereof, a methyl, ethyl and dihydroxypropyl ester thereof and δ-decalactone and one or more pharmaceutically acceptable excipients, said excipients being selected from the group consisting of physiological saline and glycols.

32. A composition for the treatment of cardiovascular diseases comprising a unit dosage form selected from the group consisting of oral preparation, injection and rectal suppository, said unit dosage containing 5–5000 mg of at least on active compound selected from the group consisting of 5-hydroxydecanoic acid, a salt thereof, a methyl, ethyl and dihydroxypropyl ester thereof and δ-decalactone and one or more pharmaceutically acceptable excipients, said composition being contained in one member selected from the group consisting of a rectal suppository, a capsule and an ampule for injection.

33. A method for the treatment of at least one cardiovascular disease comprising administering to a patient suffering from one or more cardiovascular diseases a pharmaceutically effective amount of at least one active compound selected from the group consisting of 5-hydroxydecanoic acid, a salt thereof, a methyl, ethyl and dihydroxypropyl ester thereof and δ-decalactone.

34. A method according to claim 33, wherein said at least one compound is administered in combination with one or more pharmaceutically acceptable excipients.

35. A method according to claim 33, wherein said at least one compound is administered orally.

36. A method according to claim 34, wherein said at least one compound is administered orally.

37. A method according to claim 33, wherein said at least one compound is administered by injection.

38. A method according to claim 34, wherein said at least one compound is administered by injection.

39. A method according to claim 33, wherein said at least one compound is administered on mucous membranes.

40. A method according to claim 34, wherein said at least one compound is administered on mucous membranes.

41. A method according to claim 33, wherein said at least one compound is administered at a dose of 5 to 5,000 mg/day.

42. A method according to claim 34, wherein said at least one compound is administered at a dose of 5 to 5,000 mg/day.

43. A method according to claim 35, wherein said at least one compound is administered at a dose of 100 to 5,000 mg/day.

44. A method according to claim 37, wherein said at least one compound is administered at a dose of 5 to 500 mg/day.

45. A method according to claim 39, wherein said at least one compound is administered at a dose of 5 to 500 mg/day.

46. A method according to claim 33, wherein said cardiovascular disease is at least one member selected from the group consisting of atherosclerosis, ischemic heart diseases, cardiac failure, cardiac shock, cerebral vascular diseases, peripheral vascular diseases, hypertension, arrhythmia and hyperlipidemia.

47. A method according to claim 34, wherein said cardiovascular disease is at least one member selected from the group consisting of atherosclerosis, ischemic heart diseases, cardiac failure, cardiac shock, cerebral vascular diseases, peripheral vascular diseases, hypertension, arrhythmia and hyperlipidemia.

48. A method according to claim 33, wherein said cardiovascular disease is arteriosclerosis.

49. A method according to claim 33, wherein said cardiovascular disease is selected from ischemic heart diseases.

50. A method according to claim 33, wherein said cardiovascular disease is cardiac failure.

51. A method according to claim 33, wherein said cardiovascular disease is cardiac shock.

52. A method according to claim 33, wherein said cardiovascular disease is selected from cerebral vascular diseases and peripheral vascular diseases.

53. A method according to claim 33, wherein said cardiovascular disease is hypertension.

54. A method according to claim 33, wherein said cardiovascular disease is arrhythmia.

55. A method according to claim 33, wherein said cardiovascular disease is hyperlipidemia.

* * * * *